United States Patent [19]

Hemmerich et al.

[11] Patent Number: 4,506,103

[45] Date of Patent: Mar. 19, 1985

[54] PROCESS FOR THE PREPARATION OF O-BENZYLPHENOL

[75] Inventors: Heinz-Peter Hemmerich; Werner Schulte-Huermann; Heinz Dohm, all of Krefeld, Fed. Rep. of Germany

[73] Assignee: Bayer Aktiengesellschaft, Leverkusen, Fed. Rep. of Germany

[21] Appl. No.: 529,793

[22] Filed: Sep. 6, 1983

[30] Foreign Application Priority Data

Sep. 14, 1982 [DE] Fed. Rep. of Germany ....... 3234036

[51] Int. Cl.³ .............................................. C07C 39/14
[52] U.S. Cl. .................................................. 568/744
[58] Field of Search ................................ 568/744, 747

[56] References Cited

U.S. PATENT DOCUMENTS

| | | | |
|---|---|---|---|
| 2,448,942 | 7/1948 | Winkler | 568/804 |
| 2,881,219 | 4/1959 | Thompson | 568/736 |
| 4,105,698 | 8/1978 | Stark et al. | 568/744 |
| 4,105,699 | 8/1978 | Stark | 568/744 |
| 4,117,243 | 9/1978 | Stark et al. | 568/744 |

FOREIGN PATENT DOCUMENTS 2237591 2/1974 Fed. Rep. of Germany ...... 568/804

*Primary Examiner*—Werren B. Lone
*Attorney, Agent, or Firm*—Sprung, Horn, Kramer & Woods

[57] ABSTRACT o-Benzylphenol is prepared by reacting phenol with dibenzyl ether in the presence of γ-aluminum oxide as a condensation agent.

o-Benzylphenol is used, inter alia, as such or, after chlorination, in the form of chlorobenzylphenols, as a microbicidal agent.

19 Claims, No Drawings

PROCESS FOR THE PREPARATION OF O-BENZYLPHENOL

The invention relates to a process for the preparation of o-benzylphenol by reacting phenol with dibenzyl ether in the presence of condensation agents.

A process for the preparation of aralkylphenols which is characterized in that phenols or substitution products thereof, containing a free p-position and/or o-position, are heated, in the presence of condensation agents having a catalytic action, with aralkyl ethers, dibenzyl ether being also mentioned, is known from German patent application No. 81,666 (published on 5.11.1942). The following are mentioned as condensation agents: aluminum chloride, zinc chloride, silica gel and bleaching earth.

It is a particular disadvantage in this process that it does not take place selectively, which means that, in addition to o-benzylphenol, p-benzylphenol is also formed in approximately equal parts (see Example 2 of patent application No. 81,666). In order to prepare pure o-benzylphenol, therefore, the undesired p-benzylphenol must be removed in a manner requiring technical effort.

A process for the selective preparation of o-benzylphenol is also known from U.S. Pat. No. 5,105,699. In the process described in that text, benzyl alcohol and phenol are heated in the presence of activated alumina, having an α-aluminum oxide monohydrate crystal structure, as a catalyst, o-benzylphenol being obtained virtually free from p-isomers and m-isomers. However, this process has the disadvantage that the starting material is benzyl alcohol, which is expensive, and that the yield of o-benzylphenol and the conversion of phenol are unsatisfactory for a process on a large industrial scale. Because of this, the process described in U.S. Pat. No. 4,105,699 is not very cost-effective.

A process has now been found for the preparation of o-benzylphenol by reacting phenol with dibenzyl ether in the presence of condensation agents at an elevated temperature, which is characterized in that γ-aluminum oxide is employed as the condensation agent.

The γ-aluminum oxide employed in the process according to the invention (see Gmelins Handbuch der Anorganischen Chemie (Gmelin's Handbook of Inorganic Chemistry), 8th edition, Aluminium, part B, page 78 et seq., Verlag Chemie, Berlin, 1934) has a specific surface area (BET surface area) of about 100 to 350 $m^2/g$, preferably 150 to 300 $m^2/g$. Its $Al_2O_3$ content is about 80 to 99% by weight, preferably 90 to 98% by weight. Its bulk density is about 600 to 1,100 g/liter, preferably 750 to 900 g/liter.

The quantity of condensation agent employed in accordance with the invention is generally approx. 1 to 50, preferably 3 to 20% by weight, relative to phenol employed.

In the process according to the invention, phenol and dibenzyl ether are usually employed in a molar ratio (phenol:dibenzyl ether) of about 1:0.7 to 1:0.05, preferably 1:0.45 to 1:0.1.

In this process, the reaction is carried out within the temperature range from about 100° to 300° C. The reaction is preferably carried out at 160° to 190° C. and under normal pressure.

The water of the reaction can be discharged together with a little phenol. It is then advantageous to employ a little more phenol in the reaction without thereby exceeding the phenol:dibenzyl ether molar ratios mentioned above. The water of the reaction can also be removed by adding to the reaction mixture a suitable quantity of, for example, toluene as an azeotrope-former. Examples of further suitable azeotrope-formers are benzene, xylene, heptane, octane, cyclohexane, perchloroethylene, chlorobenzene and/or nitroethane. The quantity of azeotrope-former required depends principally on the geometrical dimensions of the water separator. In general, approx. 3 to 20% by weight, preferably 5 to 15% by weight, relative to phenol employed and dibenzyl ether employed, can be regarded as a target amount.

The reaction time depends essentially on the activity of the condensation agent and on the quantity in which it is employed, and is about 3 to 50 hours, preferably 5 to 20 hours.

When the reaction is complete, the reaction mixture can be worked up by distillation, for example by vacuum distillation, if appropriate, after removing the catalyst. o-Benzylphenol is obtained in the process according to the invention in a yield of approx. 85% of theory, relative to phenol or of approx. 90% of theory, relative to dibenzyl ether. The purity of the resulting o-benzylphenol is extremely high and is at least 99%.

The process according to the invention can be carried out, for example, as follows: melted phenol, dibenzyl ether and γ-aluminum oxide are initially taken in a stirred apparatus equipped with a reflux condenser and a water separator. A suitable quantity of toluene is also added to the reaction mixture as an azeotrope-former. The reaction mixture is heated, while stirring, until a gentle reflux has been established. At the start of the reaction, the reaction temperature is about 170° C.; at the end of the reaction a temperature of approx. 190° C. is reached. The reaction is continued until approximately the theoretical quantity of reaction water has been discharged by means of the toluene. It is advantageous to follow the progress of the reaction, for example by gas chromatography. After the catalyst has been removed, for example by decanting or filtering, the reaction mixture is distilled in vacuo, and o-benzylphenol is obtained in a very high state of purity. It is also possible to carry out the vacuum distillation directly after the completion of the reaction, that is to say without previously removing the catalyst.

The process according to the invention can be carried out either continuously or discontinuously.

Compared with the state of the art, the advantages of the process according to the invention are to be seen, in particular, in the high yields and the exceptional purity of the o-benzylphenol obtained. In this respect, the particularly cost-effective mode of operation of the process according to the invention must also be borne in mind.

It is particularly surprising that, compared with German patent application No. 81,666, o-benzylphenol has been obtained at such a high degree of selectivity, using phenol and dibenzyl ether as starting materials, and that it has been possible to increase the yield of o-benzylphenol considerably, compared with the yield obtained in U.S. Pat. No. 4,105,699.

o-Benzylphenol is used, inter alia, as such or, after chlorination, in the form of chlorobenzylphenols as a microbicidal agent (see, for example: Dr. K. H. Wallhäusser and Prof. Dr. Dr. H. Schmidt in: "Sterilisation, Desinfektion, Konservierung, Chemotherapie" ("Sterilisation, Disinfection, Preservation and Chemo-

EXAMPLE 1

564.7 g (6 mols) of phenol, 356.9 g (1.8 mols) of dibenzyl ether and 45.2 g of γ-aluminum oxide having a BET surface area of approx. 240 m²/g, a loss on ignition of approx. 5% by weight and an $Al_2O_3$ content of approx. 95% by weight (bulk density approx. 860 g/liter) were initially taken in a stirred apparatus equipped with a reflux condenser and a water separator. After adding 100 g of toluene, about 26 g of water were discharged at reflux temperature (180° to 190° C.) in the course of 10 hours. After removing the aluminum oxide, 890 g of a crude product were obtained, the composition of which was determined by gas chromatography to be as follows: 23% of phenol, 0.2% of dibenzyl ether, 67% of o-benzylphenol, 0.1% of p-benzylphenol and 7% of dibenzylphenol.

The yields of o-benzylphenol which can be calculated from the gas chromatogram of the crude product amount to 84% of theory, relative to phenol, and 89% of theory, relative to dibenzyl ether. The phenol conversion amounts to 64%.

190 g of phenol were recovered when the mixture was subsequently worked up by vacuum distillation. 530 g of approx. 99% strength o-benzylphenol distilled over after an intermediate fraction of approx. 60 g. Taking account of the o-benzylphenol present in the intermediate fraction, the yields of o-benzylphenol, after distillation, are calculated to be 81% of theory, relative to phenol, and 86% of theory, relative to dibenzyl ether.

EXAMPLE 2

188.2 g (2 mols) of phenol, 99.1 g (0.5 mol) of dibenzyl ether and 19 g of γ-aluminum oxide having a BET surface area of approx. 150 m²/g, a loss on ignition of approx. 4% by weight and an $Al_2O_3$ content of approx. 94.5% by weight (bulk density approx. 850 g/liter) were initially taken in a stirred apparatus equipped with a reflux condenser and a water separator. After adding 50 g of toluene, about 8 g of water were discharged at reflux temperature (180° to 190° C.) in the course of 15 hours. After removing the catalyst, 273 g of a crude product were obtained, the composition of which was determined by gas chromatography to be as follows: 32% of phenol, 0.1% of dibenzyl ether, 62% of o-benzylphenol, less than 0.1% of p-benzylphenol and 5% of dibenzylphenol. The yields of o-benzylphenol calculated from this are: 86% of theory, relative to phenol, and 92% of theory, relative to dibenzyl ether. The phenol conversion in this case amounts to 54%.

EXAMPLE 3

1,930 g (20.5 mols) of phenol, 1,190 g (6 mols) of dibenzyl ether and 193 g of γ-aluminum oxide having a BET surface area of approx. 250 m²/g, a loss on ignition of approx. 5% by weight and an $Al_2O_3$ content of approx. 94.5% by weight were initially taken in a distillation apparatus equipped with a stirrer, and were heated up to reflux temperature under normal pressure. The water formed in the reaction could be removed by azeotropic distillation with phenol in the course of 4 hours, while the temperature in the bottom product of the reaction increased (180° to 210° C.). After removing the catalyst, 3,170 g of a crude product were obtained, the composition of which was determined by gas chromatography to be as follows: 31% of phenol, 0.3% of dibenzyl ether, 62% of o-benzylphenol, 0.2% of p-benzylphenol and 5.5% of dibenzylphenol. The yields of o-benzylphenol calculated from this are: 93% of theory, relative to phenol, and 88% of theory, relative to dibenzyl ether. The phenol conversion in this case amounts to 56%.

EXAMPLE 4

Example 1 was repeated with the exception that instead of the γ-aluminum oxide used therein α-aluminum oxide was used. For this purpose the γ-aluminum oxide was converted into the α-modification by annealing at 1200° C. for about 15 hours [Gmelin Handbuch der Anorganischen Chemie (Manual of Inorganic Chemistry), 8th edition, Aluminum, Section B, System no. 35, page 79, Verlag Chemie, Berlin, 1934]. The phase transition was confirmed by X-ray analysis.

On attempting to remove reaction water with toluene no water was obtained. After separating off the aluminum oxide 915 g of a crude product were obtained, the composition of which was determined by gas chromatography to be as follows: 59.5% of phenol, 37% of dibenzyl ether and 0.5% of o-benzyl phenol.

What is claimed is:

1. In a process for the preparation of o-benzylphenol by reacting phenol with dibenzyl ether in the presence of a condensation agent at a temperature of 100° to 300° C., the improvement wherein γ-aluminum oxide is employed as the condensation agent.

2. A process according to claim 1 wherein the condensation agent is employed in an amount of 1–50% by weight, relative to the phenol employed.

3. A process according to claim 1 wherein the condensation agent is employed in an amount of 3–20% by weight, relative to the phenol employed.

4. A process according to claim 1 wherein the γ-aluminum oxide has a specific surface area of 100–350 m²/g, and an alumina content of 80–99% by weight.

5. A process according to claim 1 wherein the γ-aluminum oxide has a specific surface area of 150–300 m²/g, and an alumina content of 90–98% by weight.

6. A process according to claim 1 wherein the process is carried out employing a phenol:dibenzyl ether molar ratio of 1:0.7–0.05.

7. A process according to claim 1 wherein the process is carried out employing a phenol:dibenzyl ether molar ratio of 1:0.45–0.1.

8. A process according to claim 1 wherein the process is carried out at a temperature of 160°–190° C. at normal pressure.

9. A process according to claim 4 wherein the alumina has a bulk density of about 600–1,100 g/liter.

10. A process according to claim 4 wherein the alumina has a bulk density of 750–900 g/liter.

11. A process according to claim 1, wherein an azeotrope-former is added during the reaction.

12. A process according to claim 11, wherein said azeotrope-former is toluene.

13. A process according to claim 11, wherein said azeotrope-former is 3 to 20 weight percent relative to said phenol and dibenzyl ether.

14. A process according to claim 11, wherein said azeotrope-former is 5 to 15 weight relative to said phenol and dibenzyl ether.

15. A process according to claim 1, wherein the reaction is conducted for 3 to 50 hours.

16. A process according to claim 1, wherein the reaction is conducted for 5 to 20 hours.

17. A process according to claim 1, wherein melted phenol, dibenzyl ether and γ-aluminum oxide are directed to a stirred apparatus, toluene is then added, the resultant reaction mixture is heated and a gentle reflux is established.

18. A process according to claim 1, wherein the temperature at the start of the reaction is 170° C.

19. A process according to claim 1, wherein the temperature at the end of the reaction is 190° C.

* * * * *